(12) United States Patent
Schneider et al.

(10) Patent No.: US 8,097,424 B2
(45) Date of Patent: Jan. 17, 2012

(54) METHOD FOR PREDICTING THE OUTCOME OF A CRITICALLY ILL PATIENT

(75) Inventors: Francis Schneider, Strasbourg (FR); Marie-Helene Metz, Strasbourg (FR)

(73) Assignee: Inserm (Institut National de la Sante et de la Recherche Medicale), Paris Cedex (FR)

( * ) Notice: Subject to any disclaimer, the term of this patent is extended or adjusted under 35 U.S.C. 154(b) by 53 days.

(21) Appl. No.: 12/602,118

(22) PCT Filed: May 29, 2008

(86) PCT No.: PCT/EP2008/056627
§ 371 (c)(1), (2), (4) Date: Nov. 27, 2009

(87) PCT Pub. No.: WO2008/145701
PCT Pub. Date: Dec. 4, 2008

(65) Prior Publication Data
US 2010/0196921 A1    Aug. 5, 2010

(30) Foreign Application Priority Data
May 29, 2007    (EP) .................................... 07109154

(51) Int. Cl.
*G01N 33/53*    (2006.01)
(52) U.S. Cl. .......................................... 435/7.1; 436/86
(58) Field of Classification Search .................... None
See application file for complete search history.

(56) References Cited

U.S. PATENT DOCUMENTS

2003/0078190 A1    4/2003   Weinberg et al.
2003/0204063 A1*  10/2003   Gravel et al. ................. 530/399

FOREIGN PATENT DOCUMENTS

WO    01/30370    5/2001

OTHER PUBLICATIONS

Wu et al. (J. Clinical Lab Anal, 1999 vol. 13, p. 312-319.*
Metz-Boutigue et al. Abstract From FENS Abstr., vol. 3, A117.7, 2006.*
International Search Report in PCT/EP08/566627, dated Nov. 10, 2008.
Estensen et al., Am. Heart J., 152:927.e1-927.e6 (2006).
Metz-Boutigue et al., FENS Abstr., vol. 3, A117.7 (2006).
Ceconi et al., Eur. Heart J., 23:967-974 (2002).
O'Connor et al., Clin. Chem., 35/8:1631-1637 (1989).
Wu et al., J. Clin. Lab. Analysis, 13:312-319 (1999).
Taupenot et al., N. Engl. J. Med., 348:1134-1149 (2003).
Lavigne et al., Intensive Care Medicine, 31(Suppl 1):S114 (2005).
Metz-Boutigue et al., Comparative Biochemistry and Physiology—Part A: Molecular and Integrative Physiology, 147 (1):20 (2007-2006).
Benedum et al., The EMBO J., 6(5):1203-1211 (1987).
International Search Report and Written Opinion in PCT/EP08/63100, dated Mar. 4, 2009.
Dai et al., Circulation,. 112(7):1008-1015 (2005).
Pannu et al., Circulation, 112(4):513-520 (2005).
Daugherty et al., Biology, 24(3):429-434 (2004).
Manning et al., Arteriosclerosis Thrombosis and Vascular Biology, 23(1):483-488 (2003).

* cited by examiner

*Primary Examiner* — Jacob Cheu
(74) *Attorney, Agent, or Firm* — McAndrews, Held & Malloy Ltd.

(57) ABSTRACT

The present invention relates to a method for predicting the outcome of a critically ill patient, said method comprising measuring the concentration of Chromogranin A or a fragment thereof in a biological sample obtained from said patient.

4 Claims, 8 Drawing Sheets

METHOD FOR PREDICTING THE OUTCOME OF A CRITICALLY ILL PATIENT

The present application is filed pursuant to 35 U.S.C. 371 as a U.S. National Phase application of International Patent Application No. PCT/EP08/56627, which was filed May 29, 2008, claiming the benefit of priority to European Patent Application No. 07109154.0, which was filed on May 29, 2007. The entire text of the aforementioned applications is incorporated herein by reference in its entirety.

FIELD OF THE INVENTION

The present invention relates to a method for predicting the outcome of a critically ill patient.

BACKGROUND OF THE INVENTION

Critically ill patients are usually admitted with clinical and biochemical signs of systemic inflammation as a consequence of their disease. These signs are ascribed to the effects of inflammatory mediators produced during the early phase response to a stress of unspecified etiology. The systemic inflammatory response syndrome (SIRS) is the clinical response traditionally associated with this biological inflammation: its incidence can be more than 50% in critically ill patients, many of whom demonstrate or will develop severe infection (Brun-Buisson. Intensive Care Med. 2000; 26 Suppl 1:S64-74). C-reactive protein (CRP) and procalcitonin are the traditional biomarkers used to evaluate the level of biological inflammation during SIRS. Despite their sensitivity and specificity for the diagnosis of infection, neither procalcitonin nor CRP give significant information as to outcome in such patients (Harbarth et al. Am J Respir Crit. Care Med. 2001; 164:396-402), who often subsequently die with multiple organ failure. Most patients surviving initial hemodynamic failure experience an insidious, progressive decline of vital organ functions, corresponding to multiple organ failure (MOF), which is associated with high and short-term mortality rates. Mortality varies from 30% to 100% even in the absence of previous health disorders.

Attempts to characterise the severity of organ failures and to predict patient outcome is of major importance for physicians in the care of critically ill patients. From an historical point of view, score building was the first step to evaluate outcome in critically ill patients because previous attempts with biological parameters failed to succeed (Schetz et al. 2005; 28:1197-210). Several outcome prediction models have been developed and are currently available in intensive care unit management, such as the APACHE (Acute Physiology and Chronic Health Evaluation) (Knaus et al. Crit. Care Med. 1981; 9:591-597), SAPS (simplified acute physiology score) (Le Gall et al. JAMA 1993; 270: 2957-63), MPM (mortality probability models) (Lemeshow et al. Crit. Care Med. 1988; 16:470-477), SOFA (Sequential Organ Failure Assessment (SOFA) (Ferreira et al. JAMA 2001; 286: 1754-58), and LOD (Logistic Organ Dysfunction) (Timsit et al. Crit. Care Med 2002; 30: 2003-13). Among these approaches, SAPS is considered as the gold standard score.

However, these prediction models have several drawbacks. First of all, a calculation of score is generally only available 24 hours after Intensive care unit (ICU) admission. Generally, more than 10 parameters shall be evaluated for determining the score. Furthermore, these scores ignore the many factors that can influence patient outcome during the course of an ICU stay. Finally, it has been shown that these scoring systems are more useful to describe and quantify organ function than to predict a real outcome. Risk assessment of patients should be based on objective variables that can be routinely measured, like biological markers.

SUMMARY OF THE INVENTION

The present invention relates to a method for predicting the outcome of a critically ill patient, said method comprising measuring the concentration of Chromogranin A or a fragment thereof in a biological sample obtained from said patient.

The present invention relates to a method for assessing the severity and/or morbidity of organ dysfunction, in particular MOF, in a patient, comprising measuring the concentration of chromogranin A (CGA) or a fragment thereof in a biological sample obtained from said patient.

The invention relates to the use of CGA or a fragment thereof as a marker of the severity and/or morbidity of critically illness.

The invention also relates to the use of CGA or a fragment thereof as a marker of the severity and/or morbidity of organ dysfunction, in particular MOF, in a patient.

DETAILED DESCRIPTION OF THE INVENTION

Definitions

The term "systemic inflammatory response syndrome (SIRS)" describes a serious condition in which there is inflammation throughout the whole body. It may be caused by a severe bacterial infection (sepsis), trauma, pancreatitis drug reactions, autoimmune disease, and other disorders. It is marked by increased heart rate, low blood pressure, low or high body temperature, and low or high white blood cell count.

The terms "sepsis", "severe sepsis" and "septic shock" are used to identify the continuum of the clinical response to infection. Patients with sepsis present evidences of infection and clinical manifestations of inflammation. Patients with severe sepsis develop hypoperfusion with organ dysfunction. Septic shock is manifested by hypoperfusion and persistent hypotension.

The terms "organ dysfunction" are defined as a clinical syndrome in which the development of progressive and potentially reversible physiological dysfunction in an organ, is characteristic even in the absence of anatomic injuries.

The term "multiple organ failure" or "MOF" denotes an organ dysfunction occurring in 2 or more organs.

The term "CGA" has its general meaning in the art and refers to Chromogranin A. Chromogranin A (CGA) is a glycophosphoprotein of 48-52 kDa, whose human form contains 439 amino acids as described by Konecki et al. J Biol Chem. 1987; 262(35):17026-30. The term may include naturally occurring CGAs and variants and modified forms thereof. The term may also refer to fusion proteins in which a domain from CGA that retains at least one CGA activity is fused, for example, to another polypeptide (e.g., a polypeptide tag such as are conventional in the art). The CGA can be from any source, but typically is a mammalian (e.g., human and non-human primate) CGA, particularly a human CGA. Exemplary human native CGA amino acid sequences are provided in GenPept database under accession numbers AAB53685, AAA52018 and Swiss Prot P10645.

The terms "fragment of CGA" refer to any natural fragments which may be present in bodily fluid: Typically the size of said fragment of CGA may be larger than 1 kDa. In a preferred embodiment of the invention, said fragment of CGA comprises amino acids 145 to 234 of human CGA.

As used herein, the term "patient" denotes a mammal, such as a rodent, a feline, a canine, and a primate. In a preferred embodiment of the invention, a patient according to the invention is a human. In a preferred embodiment of the invention, a patient according to the invention is a critically ill patient.

By "critically ill patient", it is meant a patient whose life is threatened and may therefore die within a short period of time (hours or days) as a consequence of acute organ dysfunctions.

The terms "biological sample" as used herein refer to a biological sample obtained for the purpose of in vitro evaluation. In the methods of the present invention, the sample or patient sample preferably may comprise any body fluid. Typical biological samples to be used in the method according to the invention are blood samples (e.g. whole blood sample, serum sample, or plasma sample).

Typically the biological sample may be obtained from a critically ill patient at the admission of the critically ill patient at a critical care unit or at an emergency ward.

By the terms "at the admission", it is meant within minutes of the time the patient is considered for medical care at admission in a critical care unit or at an emergency ward.

Diagnostic Methods and Kits

The present invention relates to a method for predicting the outcome of a critically ill patient, said method comprising measuring the concentration of Chromogranin A or a fragment thereof in a biological sample obtained from said patient.

The present invention relates to a method for assessing the severity and/or morbidity of organ dysfunction, in particular MOF, in a patient, comprising measuring the concentration of CGA or a fragment thereof in a biological sample obtained from said patient.

The invention relates to the use of CGA or a fragment thereof as a marker of the severity and/or morbidity of critically illness.

A further object of the invention relates to the use of CGA or a fragment thereof as a marker of the severity or morbidity of organ dysfunction, in particular MOF, in a patient.

Typically a patient according to the invention may be affected with sepsis or SIRS from non septic origin.

The inventors have found that (i) patients suffering from critical illnesses had a significant increase in blood CGA concentrations; (ii) a positive correlation between concentrations of CGA and standard biomarkers of inflammation existed in vivo; (iii) CGA concentrations were a further indication of predicting the risk of death for critically patients.

The inventors have shown a significant increase of blood CGA in acutely stressed patients compared with controls without SIRS (ie: healthy controls and self-poisoned patients without SIRS). In addition, there was a positive correlation between levels of CGA and inflammation markers. Finally, multivariable Cox proportional hazards regression demonstrated that level of CGA is a strong indicator of outcome in critically ill patients, in particular in patients affected with sepsis or systemic inflammatory response syndrome (SIRS) from non septic origin. The inventors have demonstrated that CGA significantly increases in non survivor groups that had more severe LODS or SAPS II scores. In addition, CGA concentrations were related to survival time.

The method of the invention may be thus useful for classifying a critically ill patient, in particular a patient affected with sepsis or systemic inflammatory response syndrome (SIRS) from non septic origin and then may be used to choose the accurate treatment in intensive care unit. For example, patients with a high score of severity may receive a more intensive treatment and attention compared to patient with a weak score. Such method may thus help the physician to make a choice on a therapeutic treatment which can accordingly consist in administering accurate drugs to the patients. Costs of the treatments may therefore be adapted to the severity and morbidity of the patients admitted in intensive care units, and accordingly the method of the invention may represent a useful tool for the management of such units. Finally, the method of the invention may be applied for monitoring the therapeutic outcome of a critically ill patient, in particular of a patient affected with sepsis or systemic inflammatory response syndrome (SIRS) from non septic origin.

The inventors have surprisingly demonstrated that Chromogranin A (CGA) is a marker for severity or morbidity of organ dysfunction, in particular MOF, in patients affected with sepsis or systemic inflammatory response syndrome (SIRS) from non septic origin. The ROC analysis has further demonstrated that blood CGA concentration on admission is a reliable predictor of mortality for sepsis or systemic inflammatory response syndrome (SIRS) from non septic origin, as efficient equivalent as the SAPS score. Therefore, in contrast to SAPS which requires the analysis of 17 parameters, CGA and fragments thereof represent a unique and accurate tool of determining the severity of organ dysfunction in patient affected with sepsis or systemic inflammatory response syndrome (SIRS) from non septic origin. Moreover, CGA may be easily and swiftly quantified.

Typically, the method of the invention may comprise a step of comparing the concentration of CGA or a fragment thereof with a predetermined threshold value. Said comparison is indicative of the outcome of a critically ill patient and of the severity or morbidity of organ dysfunction or MOF in said patient.

Typically said predetermined threshold value may be determined by taking into account the patient's known diseases and/or treatments which are known to elevate the blood concentration of CGA.

Examples of diseases and/or treatments known to elevate the blood concentration of CGA are pheochromocytomas, carcinoid tumors, neuroblastomas, neuroendocrine tumors, neurodegenerative diseases, chronic heart failure, acute myocardial infarction, complicated myocardial infarction, chronic renal failure, hepatic failure, ongoing steroids treatment, or ongoing proton pump inhibitors treatment, or surgical intervention.

In an embodiment of the invention, said patient is not known for being affected with a disease known to elevate the blood concentration of CGA, such as pheochromocytomas, carcinoid tumors, neuroblastomas, neuroendocrine tumors, neurodegenerative diseases, chronic heart failure, acute myocardial infarction, complicated myocardial infarction, chronic renal failure or hepatic failure.

In an embodiment of the invention, a patient according to the invention is not known for undergoing or having recently undergone a treatment known to elevate the blood concentration of CGA, such as steroids treatment, proton pump inhibitors treatment or a surgical intervention.

In an embodiment of the invention, a patient according to the invention is not a patient requiring a surgical intervention.

Once the biological sample from the patient is prepared, the concentration of CGA or a fragment thereof may be measured by any known method in the art.

For example, the concentration of CGA or a fragment thereof may be measured by using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, high performance liquid chromatography (HPLC), size exclusion chromatography, solid-phase affinity, etc.

In a particular embodiment, such methods comprise contacting the biological sample with a binding partner capable of selectively interacting with CGA or a fragment thereof present in the biological sample.

The binding partner may be generally an antibody that may be polyclonal or monoclonal, preferably monoclonal. Polyclonal antibodies directed against CGA or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against CGA can be prepared and isolated using any technique that provides for the production of antibody molecules by continuous cell lines in culture. Techniques for production and isolation include but are not limited to the hybridoma technique originally described by Kohler et al. Nature. 1975; 256(5517):495-7; the human B-cell hybridoma technique (Cote et al Proc Natl Acad Sci USA. 1983; 80(7):2026-30); and the EBV-hybridoma technique (Cole et al., 1985, In Monoclonal Antibodies and Cancer Therapy (Alan Liss, Inc.) pp. 77-96). Alternatively, techniques described for the production of single chain antibodies (see e.g. U.S. Pat. No. 4,946,778) can be adapted to produce anti-CGA, single chain antibodies. Antibodies useful in practicing the present invention also include anti-CGA fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to CGA. For example, phage display of antibodies may be used. In such a method, single-chain Fv (scFv) or Fab fragments are expressed on the surface of a suitable bacteriophage, e.g., M13. Briefly, spleen cells of a suitable host, e.g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e.g., bacteria, the phage displays the antibody fragment. Phage display of antibodies may also be provided by combinatorial methods known to those skilled in the art. Antibody fragments displayed by a phage may then be used as part of an immunoassay.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk et al. (1990) Science, 249, 505-510. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena (1999) Olin Chem. 45(9):1628-50. Peptide aptamers consist of conformationally constrained antibody variable regions displayed by a platform protein, such as *E. coli* Thioredoxin A, that are selected from combinatorial libraries by two hybrid methods (Colas et al. (1996). Nature, 380, 548-50).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the antibody, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labeling of the probe or antibody by reactivity with a detectable substance. An antibody or aptamer of the invention may be labeled with a radioactive molecule by any method known in the art. For example radioactive molecules include but are not limited radioactive atom for scintigraphic studies such as I123, I124, In111, Re186, Re188.

The aforementioned assays generally involve the bounding of the binding partner (ie. Antibody or aptamer) in a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against CGA or a fragment thereof. A biological sample containing or suspected of containing CGA or a fragment thereof is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Different immunoassays, such as radioimmunoassay or ELISA have been described in the art. For example, document U.S. Pat. No. 4,758,522 describes an immunoassay of CGA in which CGA is measured by competitive assay with radiolabelled CGA for the sites of an anti-human CGA antibody. Syversen et al (Acta Oncol. 1993; 32(2):161-5) have described an assay of chromogranin A with the ELISA technique using an antibody directed against a C-terminal fragment of CGA. Corti et al. (Br J. Cancer. 1996 April; 73(8): 924-32) have also described two assays of CGA using monoclonal antibodies directed human CGA. Document U.S. Pat. No. 6,632,624 further describes an immunoassay in which at least one monoclonal antibody specifically binds to an epitope corresponding to amino acids 145 to 234 of human CGA. Tests for detecting CGA in neuroendocrine tumors have been described by Huttner et al. (1991) Trends Biochem. Sci. 16, 27-30, Winkler et al. (1992) Neuroscience 49, 497-528, Deftos (1991) Endocr Rev 12, 181-187 and Degorce et al., (1999) Br. J. Cancer 79, 65-71. Radioimmunoassays are commercially available from CIS BIO International (30200 Bagnols/Céze—France), Alpco Diagnostics (Windham, N.H.

03087, USA), and Immuno-Biological Laboratories (Minneapolis, Minn. 55432, USA). ELISA kits for CGA are also commercially available from Alpco Diagnostics (Windham, N.H. 03087, USA) and Cosmo Bio, LTD (Tokyo 135-0016, Japan).

Another interesting approach concerns Bioplex (Biorad) using several specific CGA antibodies.

Measuring the concentration of CGA (with or without immunoassay-based methods) may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, CGA may be identified based on the known "separation profile" e.g., retention time, for that protein and measured using standard techniques. Alternatively, the separated proteins may be detected and measured by, for example, a mass spectrometer.

Yet another object of the invention relates to a kit, comprising means for measuring the concentration of CGA. The kit may include an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards. The kit may also contain one or more means for the detection of marker of organ dysfunction or infection. Typically the kit may also contain means for the detection of C reactive protein (CRP) and/or means for the detection procalcitonin (PCT) and/or means for the detection white blood cells.

A further object of the invention relates to the use of CGA or a fragment thereof as a marker of infection in a patient. An embodiment of the invention relates to a method for diagnosing an infection in a patient, said method comprising measuring the concentration of Chromogranin A or a fragment thereof in a biological sample obtained from said patient. Typically the method may further comprise detecting one or more other markers of infection such as C reactive protein (CRP) and/or procalcitonin (PCT) and/or white blood cells in a biological sample obtained from said patient.

The invention will further be illustrated in view of the following figures and examples.

FIGURE LEGENDS

Participants were 100 consecutive patients admitted to our ICU over a two-month period and 14 healthy controls from our medical staff. Patients were excluded who had former chronic renal, hepatic or cardiac failures, if they were undergoing steroids or proton pump inhibitors and if they had a medical history with neuroendocrine tumours. Finally, patients with recent multiple stress or a surgical intervention were also excluded.

Controls (SIRS− Infection−, n=23) included healthy controls (n=14) and patients with self poisoning (n=9) without SIRS; SIRS patients (SIRS+, Infection−, n=13) were those with systemic inflammatory response syndrome from non septic origin; septic patients (n=31) are in grey. The median (interquartile range) for the 3 groups were 40.0 µg/L (35.0-52.5) for controls, 110.0 µg/L (81.0-143.0) for SIRS patients and 138.5 µg/L (65-222.3) for septic patients respectively. *p<0.01, # p<0.001

Kaplan Meier analysis in the ICU patients (n=53) with infra (dotted line) or supra (full line) median values (71 µg/L). This data confirmed that the lower the plasma concentration on admission, the longer the survival time (log rank test, p=0.0013). Survival time is plotted against survival rate.

FIG. 6

Kaplan Meier analysis: cumulative incidence of death according to:

(A) chromogranin A quartiles. Median and interquartile range of CGA (ng/mL) for quartile: 35.0 (30.3-53.0); for quartile: 84.0 (76.5-93.5); for quartile 3: 174.0 (151.0-197.0); for quartile 4: 563.0 (354.5-973.8);

(B) procalcitonin quartiles. Median and interquartile range of PCT (ng/mL) for quartile 1: 0.14 (0.12-0.16); for quartile 2: 0.48 (0.36-1.01); for quartile 3: 4.82 (3.41-6.67); for quartile 4: 30.59 (18.02-43.59). Each quartile includes 30 patients.

FIG. 7

Receiver operating curve to test the ability of CGA (black line), SAPS II (black dashed line) and PCT (grey dashed line) to predict outcome.

TABLES

TABLE 1

| Characteristics | Characteristics of Participants: | | | | | |
| --- | --- | --- | --- | --- | --- | --- |
| | HC<br>n = 14 | NSNI<br>n = 9 | SIRS<br>n = 13 | S<br>n = 9 | SS<br>n = 8 | SSH<br>n = 14 |
| Age (yr) | 37.6 ± 2.8 | 64.4 ± 6.8 | 66.5 ± 5.2 | 71.9 ± 4.0 | 70.1 ± 4.4 | 69.6 ± 2.8 |
| Male sex (%) | 57.1 | 66.7 | 69.2 | 66.7 | 62.5 | 71.2 |
| Scores of severity: | | | | | | |
| SAPS$^c$ | ND | 39.2 ± 5.0 | 53.6 ± 3.9 | 39.7 ± 4.3 | 47.0 ± 2.1 | 73.4 ± 4.0** |
| LODS$^c$ | ND | 3.7 ± 1.1 | 6.9 ± 1.1* | 3.2 ± 0.8 | 5.6 ± 1 | 8.7 ± 1.0* |
| SOFA$^c$ | ND | 4.2 ± 1.4 | 6.8 ± 0.8 | 5.2 ± 1.0 | 6.5 ± 0.8 | 11.1 ± 1.0** |

TABLE 1-continued

Characteristics of Participants:

| Characteristics | HC n = 14 | NSNI n = 9 | SIRS n = 13 | S n = 9 | SS n = 8 | SSH n = 14 |
|---|---|---|---|---|---|---|
| Other indicators of severity: | | | | | | |
| Mechanical ventilation (%) | ND | 22.2 | 76.9** | 55.6 | 50 | 100** |
| Time from first organ dysfunction to admission (h) | ND | 26.7 ± 6.9 | 52.6 ± 23.6 | 57.3 ± 11.4 | 31.5 ± 10.6 | 35.4 ± 7 |
| Mean ICU stay (days) | ND | 11.9 ± 3.2 | 22.2 ± 8.6 | 11.2 ± 3.1 | 11.9 ± 3.5 | 18 ± 3.3 |
| Mortality (%) | 0 | 11.1 | 23.1 | 11.1 | 25 | 50* |
| Biomarkers | | | | | | |
| C-reactive protein (mg/L)$^c$ | 4.0 ± 0.1 | 25.2 ± 10.9 | 91.2 ± 26.9 | 84.3 ± 30.2 | 122.4 ± 44 | 109.1 ± 19.1** |
| Procalcitonin (μg/L)$^c$ | 0.04 ± 0.01 | 0.84 ± 0.51 | 3.34 ± 1.21 | 6.02 ± 4.31 | 4.44 ± 2.11 | 51.8 ± 27.5** |
| WBC counts (Giga/L)$^c$ | 7.4 ± 0.4 | 12.6 ± 0.9 | 13.9 ± 1.1 | 11.9 ± 1.9 | 18.7 ± 5.4 | 23.3 ± 7.8** |
| Creatinine (mmol/L)$^c$ | ND | 125.0 ± 19.07 | 171.6 ± 35.5 | 119.3 ± 12.4 | 141.3 ± 19.4 | 339.9 ± 61.6 |
| Chromogranin A (μg/L) | 42.7 ± 2.6 | 59.1 ± 9.8 | 119.8 ± 18.2 | 92.3 ± 20.6 | 143.2 ± 47.6 | 212.9 ± 37.9 |

Data are means ± SEM;
SAPS, Simplified Acute Physiological Score;
LODS, Logistic Organ Dysfunction Score;
SOFA, Sequential Organ Failure Assessment score;
CGA, chromogranin A;
ND: not determined;
WBC: White Blood Cells;
$^c$,significant correlation with plasma CGA levels.
*p < 0.05,
**p < 0.001

TABLE 2

| | Controls (n = 23) | | SIRS without infection (n = 13) | Infection with SIRS (n = 31) | | |
|---|---|---|---|---|---|---|
| | HC | NSNI | SIRS alone | S | SS | SSH |
| Chromogranin A (μg/L) | 39.5 (35.0-49.8) | 53.0 (34.0-92.0) | 110.0* (81.0-143.0) | 70.0* (60.0-129.0) | 77.5* (56-187.5) | 212.5** (106.8-276.5) |
| C-reactive protein (mg/L) | <4 | 7.3 (4.0-18.8) | 68.8 (20.3-96.1) | 47.7 (29.5-88.8) | 96.6 (14.9-183.3) | 105.7 (46.7-153.9) |
| Procalcitonin (μg/L) | <0.1 | 0.3 (0.1-0.5) | 0.6 (0.2-6.8) | 0.41 (0.3-5.7) | 2.1 (0.2-6.7) | 28.6 (18.0-31.6) |
| White blood cells (Giga/L) | 7.5 (6.463-8.625) | 13.4 (10.8-14.3) | 13.7 (12.3-15.7) | 8 9 (7.7-14.8) | 13.15 (11.55-17.85) | 13.6 (11.55-16.7) |
| Creatinine (μmol/L) | <50 | 107 (88-160) | 124 (87-245) | 137 (94-144) | 139 (106-170) | 233 (157.3-608.3) |

Table 2 Biological values in the study population. Data are median (interquartile range). HC stands for healthy controls, NSNI patients without SIRS or infection, SIRS patients with SIRS but without infection, S sepsis patients, SS severe sepsis patients, SSH septic shock patients. The comparisons are versus the healthy control group (HC). *p<0.05 versus HC. **p<0.001 versus HC. Significant differences are not indicated for other parameters.

Table 3

Comparison of Clinical Characteristics (3a) and Biological Markers (3b) in Survivors and Non Survivors.

Values are median (interquartile range) or percentage (frequency); n, number of cases. SAPS stands for Simplified Acute Physiological Score; LODS for Logistic Organ Dysfunction Score. The primary outcome measures were 3-month mortality.

TABLE 3a

| | Survivors (n = 87) | Nonsurvivors (n = 33) | p |
|---|---|---|---|
| Age (years) | 70 (57-79) | 70 (62-80) | 0.554 |
| Male sex (n) % | 62.1% (54) | 69.7% (23) | 0.288 |
| SAPS II score | 41 (32-53) | 70 (55-79) | <.001 |
| LODS score | 4 (2-7) | 8 (6-12) | <.001 |
| Sepsis (n) % | 50.6% (44) | 60.6% (20) | 0.219 |
| Severe sepsis (n) % | 20.7% (9) | 12.1% (4) | 0.503 |
| Septic shock (n) % | 19.5% (17) | 42.4% (14) | 0.011 |
| Cardiogenic shock (n) % | 6.9% (6) | 30.3% (10) | 0.002 |
| Time from first organ dysfunction to admission (h) | 24 (6-48) | 24 (6-72) | 0.372 |
| ICU stay (days) | 8 (4-16) | 8 (3-13) | 0.415 |

TABLE 3b

|  | Survivors (n = 87) | Nonsurvivors (n = 33) | p |
|---|---|---|---|
| Chromogranin A (ng/mL) | 86.0 (53.8-175.3) | 293.0 (163.5-699.5) | <.001 |
| C-reactive protein (mg/L) | 74.3 (24.0-151.7) | 71.7 (17.7-144.6) | 0.975 |
| Procalcitonin (ng/mL) | 0.54 (0.16-6.28) | 6.78 (2.39-22.92) | <.001 |
| White blood cells (G/L) | 13 100 (9 400-16 000) | 12 000 (5 850-18 750) | 0.459 |
| Creatinine (μmol/L) | 131 (86-220) | 186 (112-329) | 0.007 |

TABLE 4

Correlations between chromogranin A concentrationss, clinical scores, clinical parameters and biological markers.

| Variables | $r^2$ | P |
|---|---|---|
| Age | 0.360 | <0.001 |
| SAPS II score | 0.438 | <0.001 |
| LODS score | 0.374 | <0.001 |
| Time from first organ dysfunction to admission | 0.029 | 0.756 |
| ICU stay | −0.079 | 0.390 |
| C-reactive protein | 0.216 | 0.020 |
| Procalcitonin | 0.396 | <0.001 |
| White blood cells | −0.088 | 0.340 |
| Creatinine | 0.556 | <0.001 |

TABLE 5

Univariate analysis; predictors for mortality (Cox proportional hazard model)

| Variables | Hazard ratio | 95% CI | P |
|---|---|---|---|
| Age | 0.976 | 0.940-1.014 | 0.221 |
| Sex | 1.304 | 0.534-3.181 | 0.560 |
| SAPS II score | 1.042 | 1.017-1.068 | 0.001 |
| LODS score | 0.853 | 0.701-1.152 | 0.202 |
| Sepsis | 0.987 | 0.262-3.715 | 0.985 |
| Cardiogenic shock | 4.088 | 1.011-16.525 | 0.048 |
| Septic shock | 0.867 | 0.186-4.045 | 0.856 |
| Time from first organ dysfunction to admission | 1.003 | 0.996-1.010 | 0.221 |
| Log chromogranin A | 9.542 | 3.364-27.061 | <.001 |
| Log C-reactive protein | 0.712 | 0.319-1.586 | 0.405 |
| Log procalcitonin | 1.220 | 0.634-2.346 | 0.552 |
| Log white blood cells | 1.000 | 0.999-1.001 | 0.391 |
| Log creatinine | 0.584 | 0.106-3.232 | 0.538 |

TABLE 6

Multivariate analysis for the prediction of mortality (Cox proportional-hazard model).

| Variables | Hazard ratio | 95% CI | P |
|---|---|---|---|
| Log chromogranin A | 7.248 | 3.004-17.487 | <.001 |
| SAPS II | 1.046 | 1.026-1.067 | <.001 |
| Cardiogenic shock | 3.920 | 1.731-8.880 | .001 |

The hazard ratio for chromogranin A refers to log unit change. The hazard ratio for SAPS II and LODS refer to 1 unit change.

EXAMPLES

Abbreviations List

ROC: Receiver Operating Characteristic curve; AUC: Area Under Curve; CRP: C-reactive Protein; ICU: Intensive Care Unit. CGA: Chromogranin A; CRP: C-reactive protein; PCT: Procalcitonin; LODS: Logistic Organ Dysfunction System; SAPSII: Simplified Acute Physiological Score II; CI Confidence Interval; HR: Hazard Ratio; MOF: Multiple Organ Failure.

Example 1

Material and Methods

Study population: One hundred consecutive patients admitted between July and September 2006 in our intensive care unit were prospectively considered for inclusion. Fourteen healthy volunteers were recruited among staff as healthy controls (HC). Exclusion criteria comprised former chronic renal, hepatic or cardiac failure (Taupenot et al. N Engl J Med 2003; 348: 1134-49), ongoing steroids (Rozansky et al. J Clin Invest 1994; 94: 2357-68.), proton pump inhibitors (Giusti et al. Eur J Endocrinol 2004; 150: 299-303) and a medical history with neuroendocrine tumours (Berruti et al. Endocr Relat Cancer 2005; 12: 109-17). In addition, patients with recent (within 1 month) multiple stress, such as a surgical intervention were excluded.

Categorization of participants: Participants (n=114) were divided into six groups: healthy controls (HC), non septic non stressed patients (NSNI) that were comatose patients after self-poisoning requiring therefore transiently mechanical ventilation, SIRS patients that were admitted for out-of-hospital cardiac arrest without any exclusion criteria nor infection, infected patients with criteria of sepsis (S), severe sepsis (SS) or septic shock (SSH). For the diagnosis of infection, special attention was paid to the presence of fever or hypothermia, laboratory relevant positive cultures and clinical examination according to the definition of specific infection (Levy et al. Crit. Care Med 2003; 31: 1250-56).

Measurements: 10 mL of blood were withdrawn from each participant for plasma analysis. The concentrations of plasma CGA (CIS bio, Saclay, France), and several inflammatory markers procalcitonin (PCT) (Brahms, Berlin, Germany), C-reactive protein (CRP) (Dade Behring, San Francisco, USA) and white blood cell (WBC) counts were measured. Creatinin was assayed by the Jaffe reaction on an automated clinical chemistry analyzer (Dimension RxL, Dade Behring, France). Daily plasma CGA concentrations were performed during the first 3 days after ICU admission for all the surviving patients.

Scores calculation: Routine physiological and biochemical variables were recorded. Simplified Acute Physiological Score (SAPS), Logistic Organ Dysfunction Score (LODS) and Sequential Organ Failure Assessment (SOFA) score were calculated according to standards (Le Gall J R et al. 1993; Timsit J F. et al. 2002; Ferreira F L et al. 2001).

Statistical Analysis: Data are expressed as mean±SEM. SPSS was used for statistical analysis of non parametric data, including Mann-Whitney tests, One-Way Anova analysis, Spearman's Correlation test, Fisher Exact test, Repeated-Measure analysis and Receiver Operating Characteristics (ROC) curves comparisons (p<0.05 was considered to be significant).

Results

Base-line characteristics of participants: Among the 114 participants screened for enrolment 47 were rejected according to exclusion criteria and the final study population consisted of 67 whose clinical characteristics are summarized in Table 1. In septic patients (S, SS and SSH, n=31), the infection focus was the respiratory, urinary or digestive tract (n=17, 8 and 6, respectively). Gram negative bacteria were involved in 55% of the cases and Gram positive bacteria in 45%. Critically ill patients were older (p<0.05) than HC.

Within groups of patients, there were no differences as far as sex ratio, mean initial time to first organ dysfunction or mean ICU stay are concerned. SIRS and SSH patients underwent significantly more often mechanical ventilation compared with other patients (p<0.01). SSH patients have significantly higher concentrations of infection biomarkers than healthy controls (p<0.01).

Figure 1:
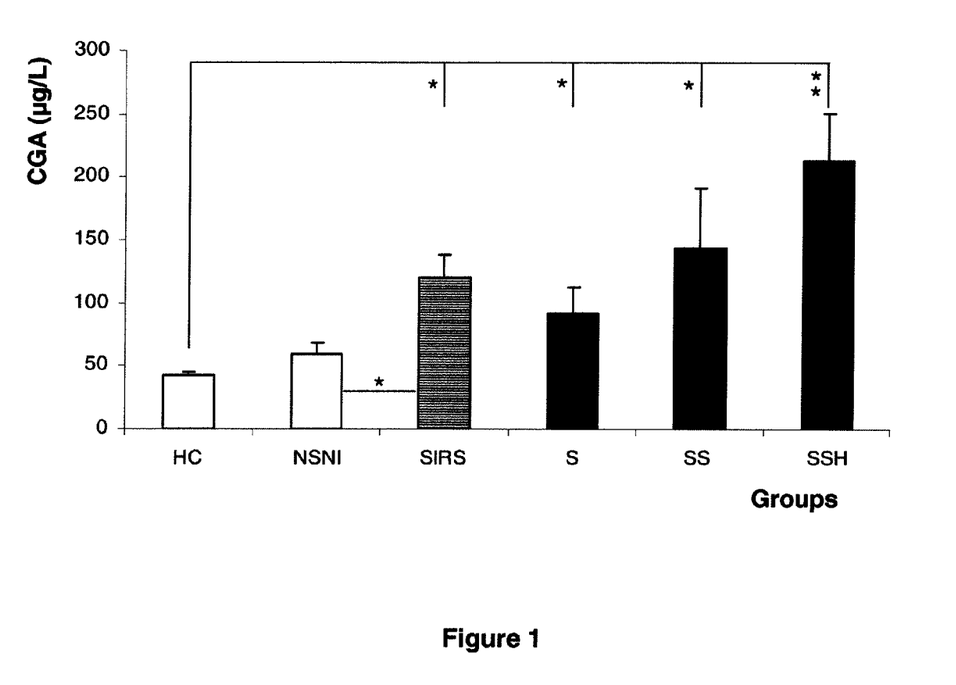
FIG. 1: Plasma Concentration of Chromogranin A on admission in Critically ill Patients and healthy controls: Data are means±SEM; *p<0.05, **p<0.01; HC: healthy controls; NSNI: patients with neither SIRS nor infection; SIRS, patients with Systemic Inflammatory Response Syndrome from non septic origin; S, patients with infection and a systemic inflammatory response syndrome; SS, severe sepsis patients; SSH, septic shock patients.

Plasma CGA concentration analysis: Plasma CGA concentration was determined using the Cis bio radioimmunoassay kit. As shown in FIG. 1, apart from NSNI, all the other groups of patients demonstrated higher CGA levels than HC (P<0.05), especially in the group SSH (P<0.01). The septic groups (S, SS, and SSH) and the SIRS group had higher CGA levels than HC and NSNI groups together (without any stress or infection) respectively (159.90±23.24 μg/L versus 49.13±4.36 μg/L, P<0.001, 119.85±18.22 μg/L versus 49.13±4.36 μg/L, P<0.05). In contrast, there was no difference in CGA levels between the septic and SIRS groups.

Repeated measurement analysis of CGA over the first 3 days after ICU admission indicated that CGA levels did not significantly change in any of the patient categories (P>0.05).

Relationship between CGA, inflammation and scores: Spearman's correlation analysis showed (Table 1) that CGA plasma level had a significant positive correlation with procalcitonin (R=0.809, p<0.01), C-reactive protein (R=0.745, p<0.01), creatinin (R=0.709, p<0.01), WBC counts (R=0.553, p<0.05), SAPS(R=0.636, p<0.01), SOFA (R=0.524, p<0.05) and LODS (R=0.546, p<0.05).

Relationship between CGA concentrations and the final outcome with MOF: As shown in Table 1, MOF has been demonstrated for all the patients who died in our study, as proven by organ failure scores. SSH had higher mortality than other patients (P<0.05). In the non survivor group, CGA on admission was twice as high as in the survivor group (206.2±26.8 μg/mL versus 106.7±16.5 μg/mL, p<0.001). As expected, SSH patients had significantly worse SAPS and SOFA scores than others (p<0.01); as far as LODS is concerned, there was no significant difference between SSH and SIRS patients, but both categories had significantly poorer scores than other patients (p<0.05).

Statistical analysis showed that in diverse MOF severity patients (indicated by SAPS), plasma CGA concentrations were significantly different. Thus, CGA concentrations of patients with SAPS greater than 60 were higher than patients with SAPS between 40 and 60 (P<0.001). In this second group CGA was also higher than in patients with SAPS less than 40 (P<0.01); furthermore CGA increased during the development of MOF in sepsis.

Figure 2:
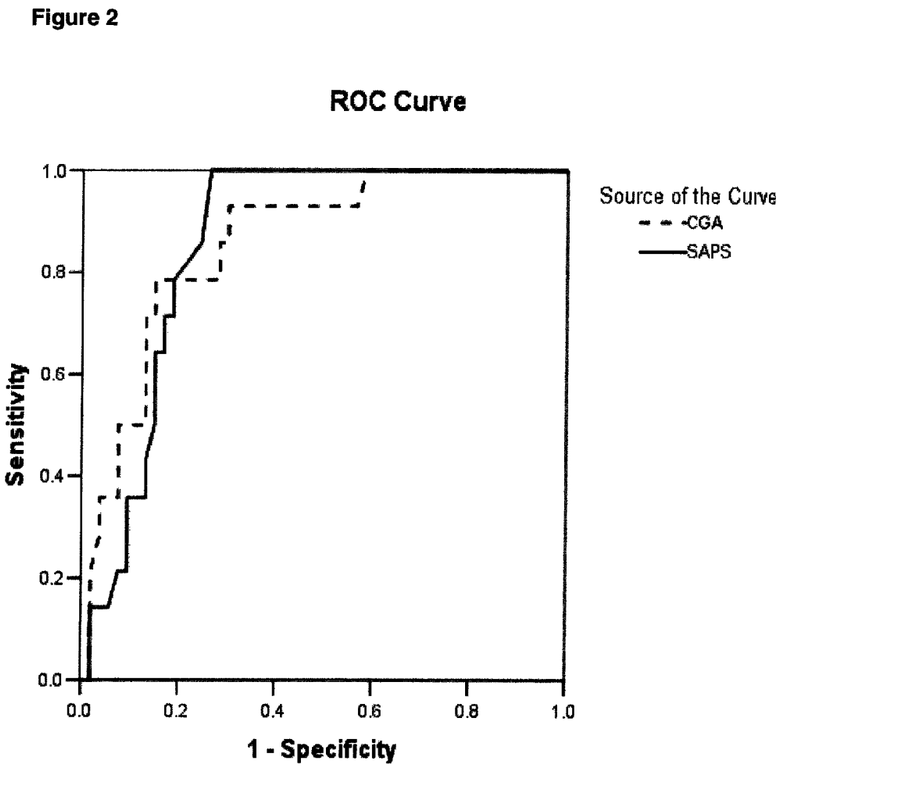
FIG. 2: ROC curve comparing the plasma CGA on admission and the SAPS for predicting death with MOF.

ROC analysis showed that CGA was a strong predictor for mortality with MOF in sepsis, comparable to the SAPS (AUC 0.810, 95% CI 0.680-0.939, 0.698-0.923 respectively (FIG. 2), and was superior to other routine scores such as SOFA and LODS (AUC 0.750, 95% CI 0.609-0.891 for SOFA; AUC 0.697, 95% CI 0.552-0.842 for LODS). For a cut-off value of 132 μg/mL, the sensitivity of CGA to predict death was 78.6% and its specificity 79.5%. Finally, ROC analysis for the prediction of infection indicated that CGA gives diagnostic value for infection as efficiently as procalcitonin or C-reactive protein.

Example 2

Plasma Concentration of Chromogranin A at Admission: an Early Biomarker of Severity in Critically Ill Patients Abstract Aim. To determine evidence for a link between plasma concentration of CGA, biomarkers of inflammation and outcome in patients admitted with or without a Systemic Inflammatory Response Syndrome (SIRS).

Methods. At admission, we measured the plasma concentrations of CGA, procalcitonin and C-reactive protein, and we assessed the Simplified Acute Physiological Score (SAPS) in 53 patients.

Results. Plasma CGA concentrations were significantly increased in SIRS patients with a median value of 115 μg/L (68.0-202.8), when compared to healthy controls (p<0.001). In cases where infection was associated with SIRS, patients had the highest increase in CGA with a median value of 138.5 μg/L (65-222.3) (p<0.001). CGA concentrations positively correlated with inflammation markers (procalcitonin, C-reactive protein), but also with SAPS. Receiver Operating Characteristic (ROC) analysis showed that CGA is equivalent to SAPS as an indicator for 28-day mortality (Area Under Curve, AUC for both 0.810).

Conclusions. Patients with CGA plasma concentration superior to 71 μg/L have a significantly shorter survival. A Cox model confirmed that CGA and SAPS were independent predictors of outcome.

Materials, Patients and Methods

Figure 3:
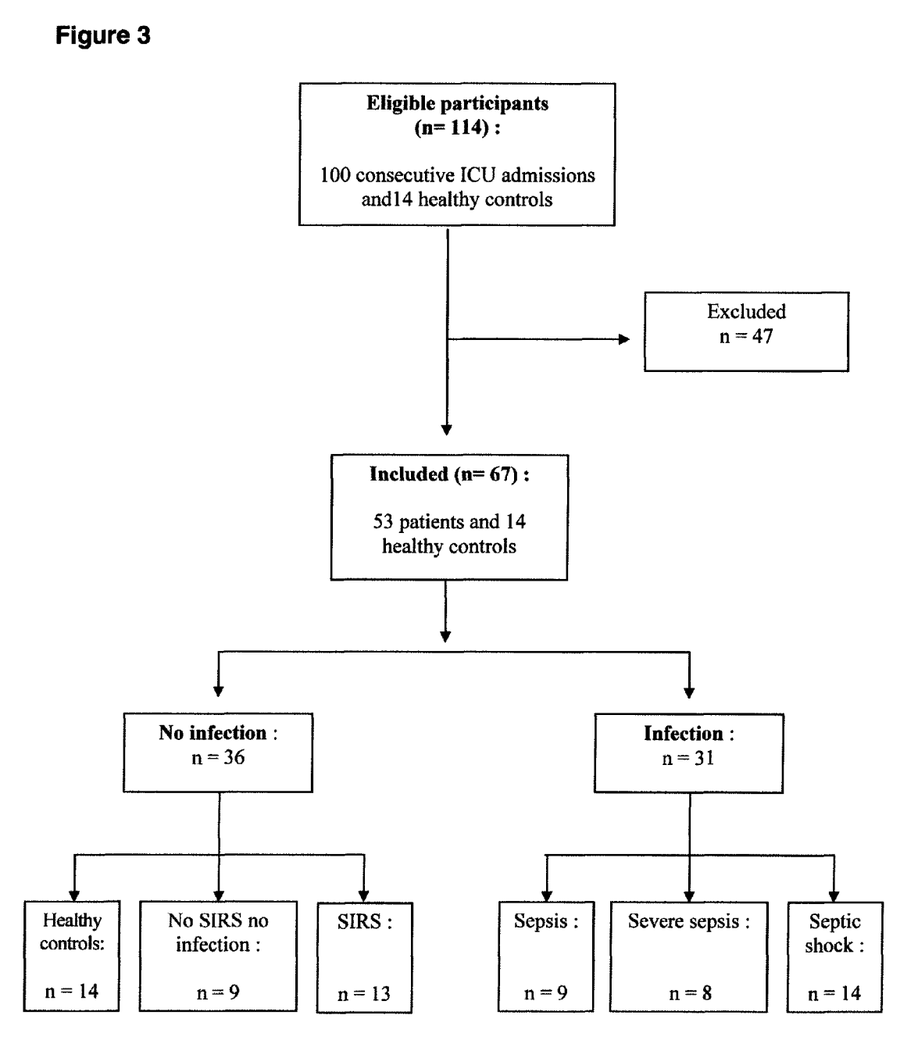
FIG. 3: Flow chart of the study
Figure 4:
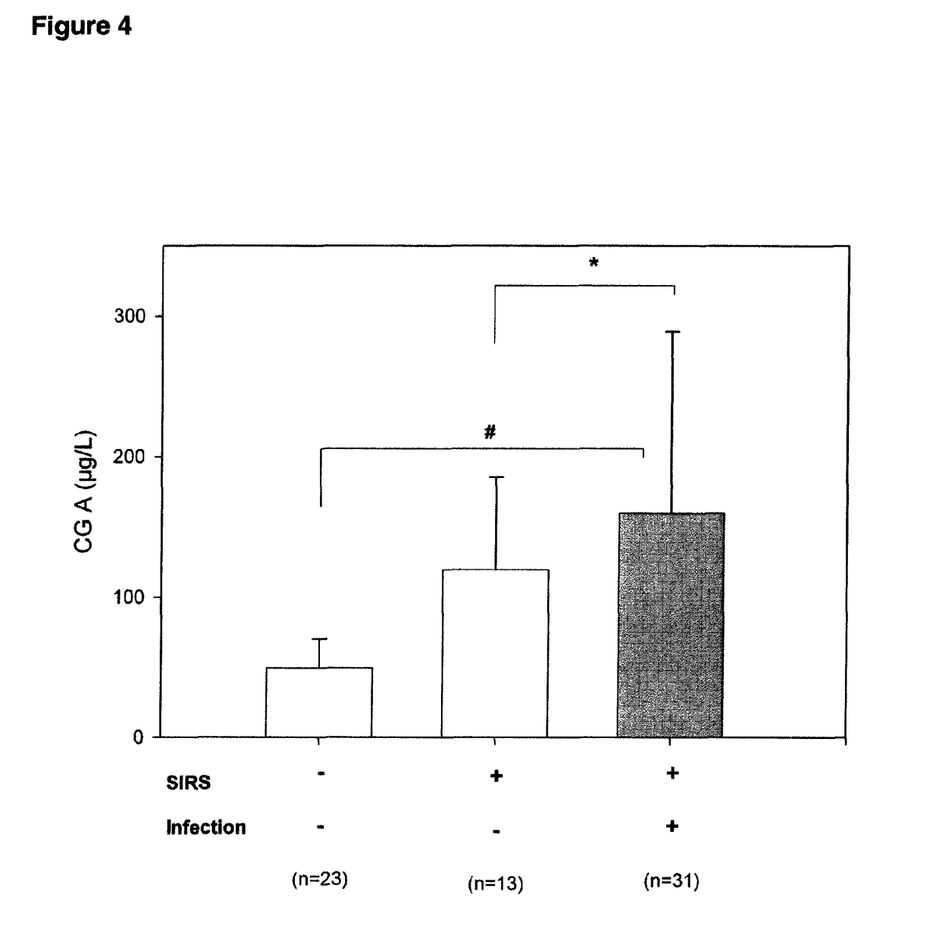
FIG. 4: Plasma concentrations of CGA on admission in critically ill patients

Study population. This study protocol was approved by our institutional review board for human experimentation. Written informed consent was obtained before enrolment from each participant or authorized representative. One hundred consecutive patients admitted over two months in our department were prospectively considered for inclusion: only 53 of them could be included due to exclusion criteria, five patients corresponding to chronic renal (previous history of kidney disease and documented clearance of creatinine less than 60 mL/min), hepatic (with a previous history of liver disease and/or an abnormality of liver tests) or cardiac failure (with an history of heart disease and/or a pulmonary artery occlusion pressure over 16 mm Hg with cardiac output in the range of normal values), ongoing steroids (nine patients), proton pump inhibitors (ten patients) and a medical history of neuroendocrine tumours (five patients). Patients with surgical intervention within one month were also excluded. Fourteen healthy volunteers were finally recruited among staff as healthy controls. The flow chart of the study is shown in FIG. 3.

Participants were divided into two groups:
1) non septic participants that included i) healthy controls (HC); ii) patients without SIRS and without infection (NSNI) that were patients with benzodiazepines and/or neuroleptic drugs self-poisoning requiring mechanical ventilation; iii) SIRS patients that were admitted for out-of-hospital cardiac arrest without any other exclusion criteria;
2) Septic patients with infection and SIRS including i) sepsis (S), ii) severe sepsis (SS) and iii) septic shock (SSH) patients. For the diagnosis of infection, special attention was paid to the presence of cultures positive for bacteria.

Patients were volume resuscitated and managed according to consensual care (Antonelli et al. Intensive Care Med. 2007; 33:575-90).

Measurements. We measured the concentrations of plasma CGA (CIS bio, Saclay, France), procalcitonin (PCT) (Brahms, Berlin, Germany), C-reactive protein (CRP) (Dade Behring, San Francisco, USA), white blood cell (WBC) counts and creatinine. SAPS was calculated according to standards. Mortality was assessed on Day 28 after ICU admission.

Statistical Analysis

Results are expressed as means+/−SEM for continuous variables except for biological values that are expressed in medians and interquartile ranges. Statistical analysis was carried out using Mann-Whitney test for continuous variables and Fisher's exact test for categorical variables. Multivariate analysis was used when necessary. Correlations were performed by Spearman rank test. Receiver operating characteristics (ROC) curves were constructed for predicting mortality; the areas under the curve were calculated, and ROC curves were compared. Finally a Kaplan Meier analysis of survival was performed. In all cases, $p<0.05$ was considered to be significant.

A Cox proportional hazard regression model was used to evaluate the effect of CGA levels on the endpoint and calculate hazard ratios with 95% confidence intervals (CI). To assess the independent prognostic value of CGA, a backward elimination procedure was first used.

Results

Characteristics of participants. The final study population consisted of 67 participants whose clinical and biological characteristics are shown in Table 1 and Table 2 respectively. In septic patients (n=31), the infection focus was the respiratory apparatus, the urinary or biliary tracts (n=17, 8 and 6, respectively). Gram negative bacteria were involved in 55% of the cases and Gram positive bacteria in 45%. Healthy controls were younger than intensive care unit (ICU) patients ($p<0.05$). Within subgroups of patients, there were no differences as far as age, sex ratio, mean time from starting stress to first organ dysfunction or mean ICU stay were concerned. SIRS and SSH patients underwent significantly more often mechanical ventilation compared with others ($p<0.01$). SSH patients had significantly higher concentrations of infection biomarkers than healthy controls ($p<0.01$).

Plasma CGA concentrations study. On admission, acutely stressed patients with a SIRS (including both septic patients and patients with SIRS but without infection, n=44) had significantly higher plasma concentrations of CGA than controls (115 µg/L (68-202.8) versus 40 µg/L (35-52.5), $p<0.001$). As indicated in Table 2, all the subgroups of patients demonstrated higher CGA levels than healthy controls ($p<0.05$), apart from patients without either SIRS or infection. The septic group (S, SS, and SSH) had significantly higher CGA levels than patients with SIRS but without infection (138.5 µg/L (65-222.3) versus 110 µg/L (81-143), $p<0.01$).

Relationship of CGA with inflammation markers, SAPS score and outcome. CGA plasma levels positively correlated with biomarkers of inflammation (C-reactive protein $r^2=0.555$, $p<0.01$, procalcitonin $r^2=0.655$, $p<0.01$, and white cell counts $r^2=0.306$, $p=0.012$) and also with creatinine ($r^2=0.503$, $p<0.01$) and with SAPS ($r^2=0.405$, $p=0.003$). Multivariate analysis indicated that creatinine and age were independent factors for the level of CGA, but neither SIRS nor infection were. Septic shock patients had a higher death rate than other patients ($p<0.05$). In the non survivor group, CGA on admission was three times as high as in the survivor group (192.5 (145.8-285.8) µg/L versus 65.0 (36.0-94.0) µg/L, $p<0.001$). As expected, septic shock patients had significantly worse SAPS scores than others ($p<0.01$). Finally, comparison of areas under the ROC curves showed that the plasma CGA level at admission was as efficient as the SAPS in predicting mortality in our study population (for both AUC 0.810, 95% CI 0.680-0.939 for CGA and 0.698-0.923 for SAPS, respectively). For a cut off value of 139 µg/L, the sensitivity of CGA to predict death was 78.6% and its specificity 79.5%.

Figure 5:
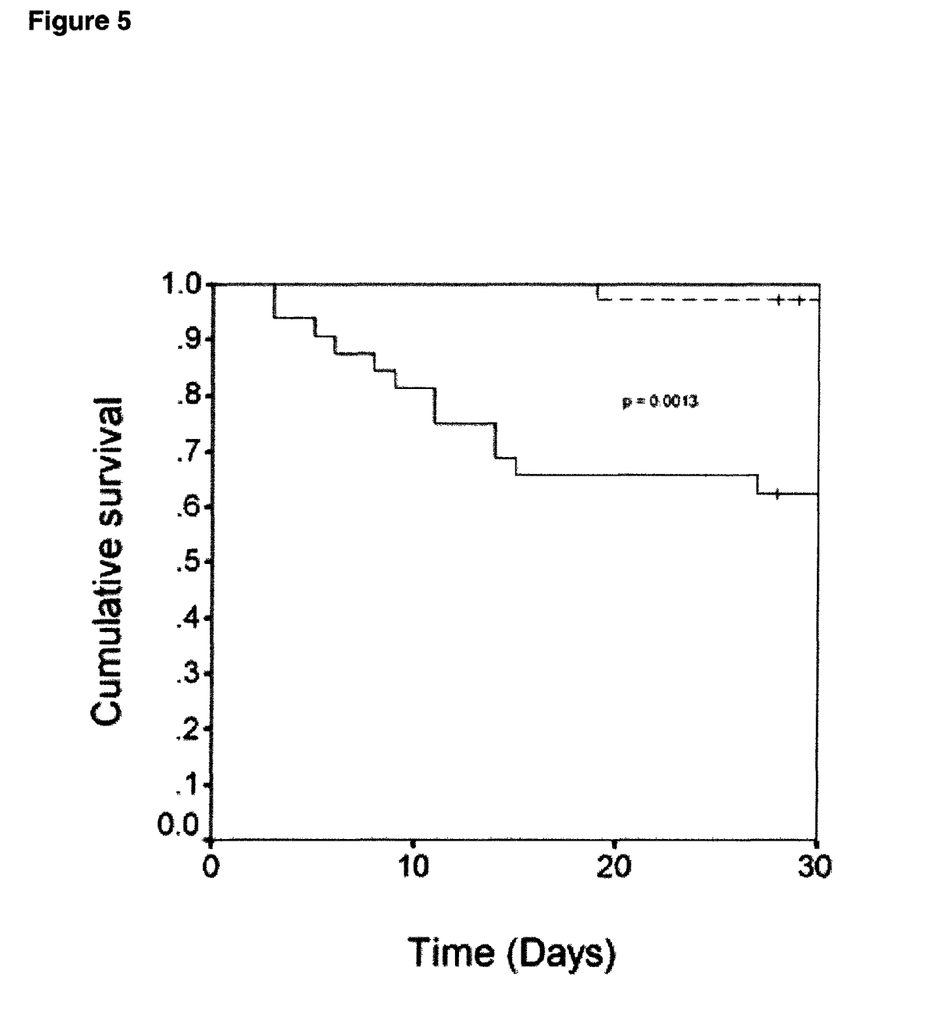
FIG. 5: Influence of plasma CGA concentration at admission on survival time
Figure 6:
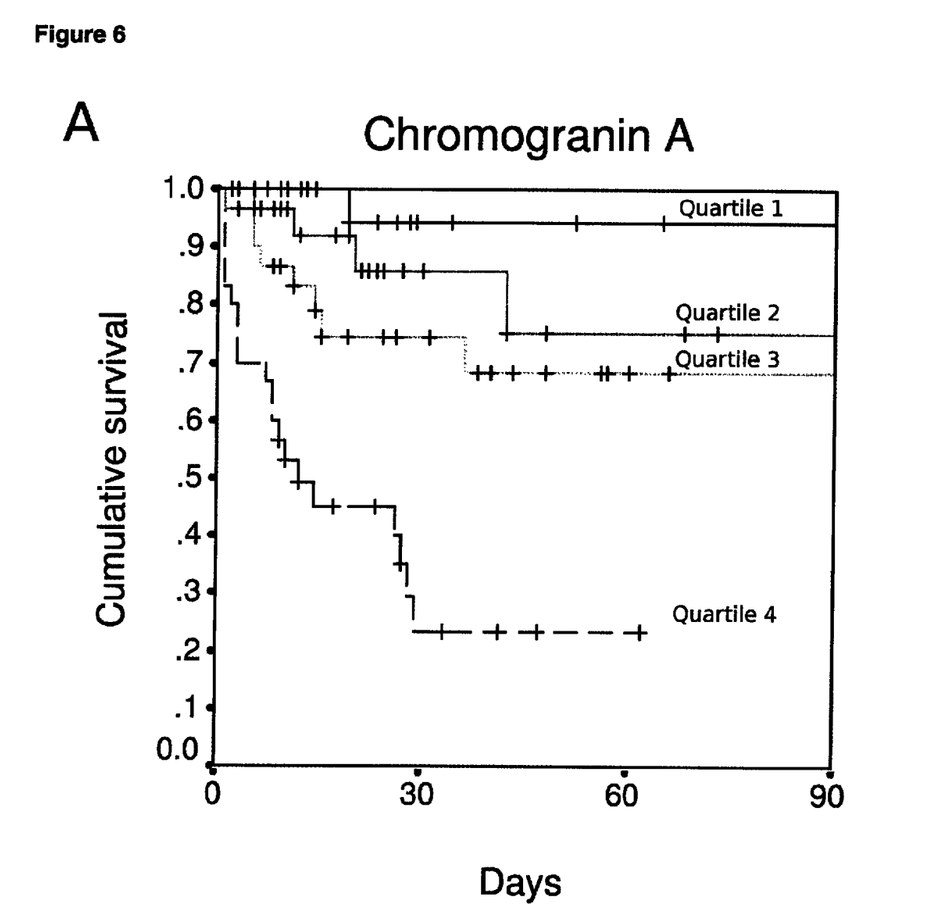

As shown in FIG. 5, the Kaplan Meier analysis indicated that the admission value of CGA was significantly associated with the survival time: patients with supramedian levels of CGA (>71 µg/L) had significantly shorter survival time (p=0.0013). By multivariable Cox proportional hazards regression, CGA levels (Hazard ratio (HR)=1.022, CI: 1.012-1.051 and SAPS II (HR=1.025, CI: 1.015-1.054) at admission were significantly associated with outcome ($p<0.05$).

Discussion

In this study, we found that (i) patients suffering from critical illnesses had a significant increase in plasma CGA concentrations: a fact which has previously never been reported; (ii) a positive correlation between plasma concentrations of CGA and standard biomarkers of inflammation existed in vivo; (iii) CGA plasma concentrations were a further indication of predicting the risk of death in these non-surgical ICU patients. We also show a significant increase of plasma CGA in acutely stressed patients compared with controls without SIRS (ie: healthy controls and self-poisoned patients without SIRS).

Relationship between CGA and outcome. In this study, correlations between CGA and SAPS were obtained. Thus, for each range of SAPS, plasma CGA significantly increased. In addition, CGA concentrations were related to survival time (FIG. 5), Currently, the way to predict outcome of critically ill patients is organ failure score calculations. On this approach, SAPS is considered as the gold standard score. The ROC analysis demonstrated that plasma CGA concentration on admission is a reliable predictor of 28-day mortality for critically ill patients. It is as efficient as the SAPS score, but the SAPS requires the analysis of 17 clinical and biochemical parameters to make an accurate prediction 24 h after admission. CGA measured on admission enables physicians to predict more easily and earlier an ominous outcome

CONCLUSIONS

We have shown an increase of plasma CGA levels in non-surgical critically ill patients and a significant correlation between CGA concentrations, the inflammation biomarkers and the outcome. Our present study suggests the opportunity for improving the care management of critically ill patients by measuring the CGA concentration at admission.

Example 3

Prognostic Value of Chromogranin A at Admission in Critically Ill Patients: a Cohort Study in a Medical Intensive Care Unit Abstract Methods: We conducted a prospective study in such patients to measure serum procalcitonin (PCT), C-reactive protein (CRP) and CGA obtained at admission. Univariate and multivariate analyses were performed to identify the ability of these biomarkers to predict mortality.

Results: In 120 consecutive patients a positive correlation was found between CGA and CRP ($r^2=0.216$, $p=0.02$) and PCT ($r^2=0.396$, $p<0.001$) and Simplified Acute Physiologic Score II (SAPSII) ($r^2=0.438$, $p<0.001$) and Logistic Organ Dysfunction System (LODS) ($r^2=0.374$, $p<0.001$). Non survivors had significantly higher CGA and PCT values than survivors (median (interquartile range) of 293.0 ng/mL (163.5-699.5) versus 86.0 ng/mL (53.8-175.3) for CGA, and 6.78 ng/mL (2.39-22.92) versus 0.54 ng/mL (0.16-6.28) for PCT, $p<0.001$). In multivariable linear regression analysis, creatinine ($p<0.001$), age ($p<0.001$) and SAPSII ($p=0.002$) were the only independent variables predicting CGA levels ($r^2=0.352$). In multivariate analysis, 3 independent factors were involved in death prediction: log-normalized CGA levels (hazard ratio (HR)=7.248, 95% confidence interval (CI) 3.004-17.487), SAPSII (HR=1.046, 95% CI 1.026-1.067) and cardiogenic shock (HR=3.920, 95% CI 1.731-8.880).

Conclusions: CGA is a strong and independent indicator of prognosis in non surgical critically ill patients.

Methods

Study Population

This study protocol was approved by our institutional review board for human experimentation; written informed consent was obtained before enrolment from each participant or authorized representative. Patients over 18 years were recruited consecutively over 3 months. Exclusion criteria were (1) a duration of stay <24 h, and (2) conditions known to increase CGA levels independently of acute stress (ie: an history of documented neuroendrocine tumors and chronic treatment with proton pump inhibitors before admission. We also did not include patients requiring surgical interventions.

Processing of Blood Samples

Blood samples were collected at admission by venipuncture into serum separator tubes without anticoagulant (Becton Dickinson). The tubes were immersed in ice and immediately transported to the laboratory for processing. Serum was separated by centrifugation (1500 g for 15 min) at 4° C. and stored in 200 µL aliquots at −80° C. until analysis. All samples were stored and processed identically to ensure uniformity of measurements.

Measurements

Serum C-reactive protein (CRP) was measured by a turbidity assay against controls and serum creatinin was measured using the Jaffe method, as specified by the manufacturer (Behring Diagnostics). Serum CGA concentrations were measured with a commercial sandwich radioimmunoassay (CIS BIO), with 125I-labeled CGA bioactive as a tracer molecule and two monoclonal antibodies against human CGA amino acid sequences 145-197 and 198-245. In our assay, the intra- and inter assay CVs were 5.9% and 7.7%, respectively (15 replicates of a human serum pool with a mean concentration of 32 ng/mL). In 95% of the population, serum CGA levels range from 19.4 ng/ml to 98.1 ng/ml. In neuroendocrine system tumors, the CGA serum level varies from normal up to 1200 ng/ml depending on the biological and structural characteristics of the tumor, as well as extension of tumors (Giovanella et al. Int J Biol Markers 1999; 14:160-6). The concentrations of PCT were determined by the time-resolved amplified cryptate emission methodology on Kryptor (Brahms Diagnostic), following the assay manufacturer's recommendations. White blood cell count (WBC) was measured by an LH 700 automated blood cell counter (Beckman Coulter).

Clinical Data

The diagnoses were all performed on admission. We defined septic shock and severe sepsis according to the criteria set by the International Sepsis Definition Conference Levy et al Crit. Care Med 2003; 31:1250-6). Cardiogenic shock was diagnosed after documentation of myocardial dysfunction, and exclusion or correction of factors such as hypovolemia, hypoxia, and acidosis, according to the definition by Forrester et al. N Engl J Med 1976; 295:1404-13. Simplified Acute Physiological Score II (SAPS II) and Logistic Organ Dysfunction System (LODS) were calculated at admission according to standards.

Outcome

The primary outcome measures were 3-month mortality.

Statistical Analyses

Continuous data are reported as the median (interquartile range) and group differences were compared by Mann-Whitney U- or Kruskal-Wallis tests. Kolmogorov-Smirnov test was used to test the normality of the variables. Categorical variables are reported as the frequency (percentage), and differences between groups were tested by $Chi^2$ test. Correlation analyses were performed by Spearman rank test. Multiple linear regression analysis using backward stepwise selection procedures to exclude those variables with p values >0.05 was built, and p values were calculated using the Wald test. A Kaplan Meier analysis of survival was performed for the most significant variables. A Cox proportional hazard regression model was used to evaluate the effect of logarithmically transformed CGA on the endpoint and calculate hazard ratios with 95% confidence intervals (CI). To assess the independent prognostic value of CGA, a backward elimination procedure was first used. In all cases, p<0.05 was considered to be significant. We computed a receiver-operated curve to explore the relationship between the sensitivity and specificity of the prognostic with the biomarkers and a receiver-operated curve to identify the ability of these biomarkers to diagnosis septic patients vs non septic patients, i.e. infection vs inflammation. All statistical analyses were performed with the SPSS statistical package (SPSS for Windows version 11.5).

Results 155 patients were screened for this study and 35 patients were excluded: 32 patients because duration of stay was <24 h (19 self poisoning, 3 deaths within 24 h, 9 venous central line catheterism, 1 patient because of chronic pump inhibitor treatment) and 3 patients because of history of neuroendocrine tumors.

Base-Line Characteristics of Participants

The final study population consisted of 120 participants whose clinical characteristics are summarized in Table 3a and 3b. Non survivors (n=33) had significantly higher LODS and SAPS II scores than survivors (n=87) and there were significantly more patients with septic shock and cardiogenic shock in the non survivor group than in the survivor group (Table 3a). As far as biological markers are concerned, non survivors had significantly higher levels of creatinine, PCT and CGA (Table 3b). However, there were no differences as far as age, white blood cell counts or C-reactive protein levels were concerned.

Relationship Between CGA and Clinical Scores and Biomarkers

Spearman's correlation analysis showed (Table 4) that CGA levels positively but weakly correlated with age and PCT, and creatinine, and SAPS II, and LODS (p<0.001 for all these variables), and C-reactive protein (p=0.02). All these variables were entered into a multiple linear regression model using a stepwise backward elimination. 35.2% ($r^2$=0.352) of the variability in CGA levels could be explained by creatinine (p<0.001), age (p<0.001) and SAPS II (p=0.002). Identical results were obtained using a stepwise forward selection procedure.

Chromogranin A and Diagnosis

We generate ROC to identify the ability of our biomarkers to diagnosis septic patients vs non septic patients. For this, we choose a cut-off value that optimized sensibility. For PCT with a cut-off value of 0.34 ng/mL sensitivity is 0.80 and specificity 0.44. The area under the curve is equal to 0.70. For CRP with a cut-off value of 44 mg/L sensitivity is 0.80 and specificity 0.55. The area under the curve is 0.72. For CGA with a cut-off value of 88.5 ng/mL sensitivity is 0.61 and specificity 0.45. The area under the curve is 0.56. There's a statistical difference between area under the curve of CGA vs PCT or CRP (p<0.001).

Chromogranin A and Prognosis

During a median follow-up time of 23 days, there were 33 deaths. The death rate according to quartiles of CGA and PCT are shown respectively in FIGS. 5a and 5b. Statistical analysis showed significant difference between CGA quartile 4 versus CGA quartiles 1, 2 and 3 (p<0.001, log-rank test), and CGA quartile 3 versus CGA quartile 1 (p=0.033). For PCT, we found a difference between quartile 4 versus quartile 1, 2 and 3 (p<0.001) and quartile 2 versus quartiles 3 and 4 (p<0.05). Unadjusted HR with 95% CI for the association between potential variables for the prediction at baseline and the risk of death are presented in Table 5. By multivariable Cox proportional hazards regression, log CGA levels, SAPS II and the diagnosis of cardiogenic shock at admission were significantly associated with outcome. Table 6 shows the adjusted HR of independent variables for the prediction of mortality.

Figure 7:
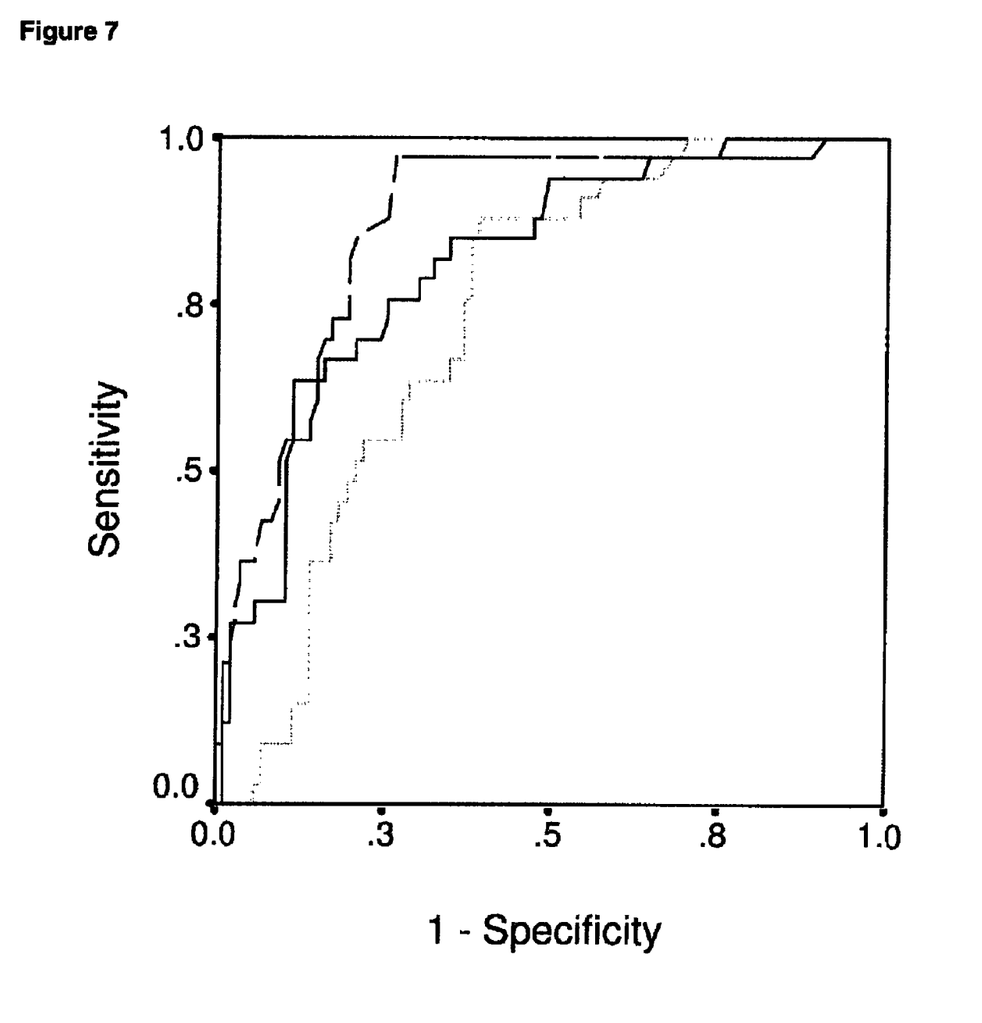

Receiver operating curve have been generated for CGA, PCT and SAPSII (FIG. 7). To assess the best positive likelihood ratio, we choose the cut-off value which is associated with the best specificity. For CGA, we choose a cut-off value of 254.5 ng/mL leading to a sensitivity of 0.63 and a specificity of 0.89. In this case, the positive likelihood ratio is equal to 5.73, the negative likelihood ratio is equal to 0.42. The area under the curve is equal to 0.82. For SAPS II with a cut-off value of 65, sensitivity is equal to 0.61 and specificity 0.85; the positive likelihood ratio is equal to 4.07, the negative likelihood ratio is equal to 0.46. The area under the curve is equal to 0.87. For PCT with a cut-off value of 4.82 ng/mL sensitivity is equal to 0.60 and specificity 0.71; the positive likelihood ratio is equal to 2.07, the negative likelihood ratio is equal to 0.56. The area under the curve is equal to 0.73.

Discussion

In this study, we found a significant increase in plasma CGA concentrations in non surgical critically ill patients not selected for their medical disease but for the severity of its presentation on admission. Such a finding has never been reported. In addition, there was a positive correlation between levels of CGA and inflammation markers. Finally, multivariable Cox proportional hazards regression demonstrated that level of CGA is a strong indicator of outcome in our cohort of patients.

Influence of Acute Renal Failure on CGA Levels.

Accumulation of CGA in end-stage chronic renal disease has been reported previously but the impact of acute renal failure on circulating CGA levels in critically ill patients observed in our study is a new finding.

Pathophysiological Role of CGA in Critically Ill Patients.

Our data have demonstrated that CGA significantly increases in non survivor groups that had more severe LODS or SAPS II scores. In addition, CGA concentrations were related to survival time.

Relationship Between CGA and Outcome.

In our study, we found that CGA level at admission is a powerful and early marker of prognosis. Compared to others markers, CGA had the highest positive likelihood ratio (5.72 vs 4.07 for SAPS II or 2.07 for PCT). CGA could be measured at admission easily in every institution and may therefore be helpful for physicians in predicting ominous outcome.

When PCT was proposed for such an evaluation in severely ill patients, it rapidly became clear that PCT was a breakthrough in the diagnosis of infection when compared to other available biological tests. On the other hand, controversial data exist on the ability of PCT to predict outcome in patients with SIRS. In our experiment, CGA turned out to be a much better predictor than PCT for outcome even though CGA could not discriminate between inflammation and infection compared to PCT or CRP.

Conclusions

The present study demonstrates that plasma CGA concentration is a strong and independent prognostic marker in consecutive non surgical critically ill patients. Thus this biomarker may help physicians to categorize patients for further care or for the selection for clinical studies.

References

Throughout this application, various references describe the state of the art to which this invention pertains. The disclosures of these references are hereby incorporated by reference into the present disclosure.

The invention claimed is:

1. A method for predicting the survival outcome of a critically ill patient, said method comprising measuring the concentration of Chromogranin A (CGA) in a biological sample obtained from said patient wherein an elevated level of CGA in said critically ill patient as compared to the level of CGA in control patient predicts a shorter survival for said critically ill patient as compared to said control patient wherein said patient is affected with sepsis or systemic inflammatory response syndrome (SIRS) from non septic origin.

2. The method according to claim 1, wherein said biological sample is a whole blood sample, a serum sample or a plasma sample.

3. The method according to claim 1, wherein said patient is not a patient requiring a surgical intervention.

4. The method according to claim 1, wherein said patient is not a patient known for being affected with a disease known to elevate the blood concentration of CGA, or wherein said patient is not a patient known for undergoing or having recently undergone a treatment known to elevate the blood concentration of CGA.

* * * * *